United States Patent [19]
Young et al.

[11] Patent Number: 5,827,316
[45] Date of Patent: Oct. 27, 1998

[54] ROTATING AORTIC PUNCH

[75] Inventors: Larry Lee Young, Arab; Rowland W. Kanner, Guntersville, both of Ala.

[73] Assignee: Atrion Medical Products, Inc., Arab, Ala.

[21] Appl. No.: 872,761

[22] Filed: Jun. 5, 1997

[51] Int. Cl.$^6$ .................................................. A61B 17/34
[52] U.S. Cl. ........................ 606/185; 606/180; 606/184
[58] Field of Search .................................. 606/180, 185, 606/170, 184, 187

[56] References Cited

U.S. PATENT DOCUMENTS

| | | |
|---|---|---|
| D. 372,310 | 7/1996 | Hartnett . |
| 4,018,228 | 4/1977 | Goosen . |
| 4,216,776 | 8/1980 | Downie et al. . |
| 5,129,913 | 7/1992 | Ruppert . |
| 5,192,294 | 3/1993 | Blake . |
| 5,403,338 | 4/1995 | Milo . |
| 5,488,958 | 2/1996 | Topel et al. ............................. 606/184 |
| 5,643,305 | 7/1997 | Al-Tameem ............................. 606/180 |
| 5,693,064 | 12/1997 | Arnold .................................... 606/184 |

*Primary Examiner*—Michael Powell Buiz
*Assistant Examiner*—Kevin Truong
*Attorney, Agent, or Firm*—Trexler, Bushnell, Giangiorgi & Blackstone, Ltd.

[57] ABSTRACT

Disclosed is a novel aortic punch having a cutter on the end of a hollow body member. The hollow body member is slidable along a non-rotating shaft. On the end of the shaft is an anvil, and helical drive structure is provided between the hollow body member and the shaft or another non-rotating element adjacent the hollow body member. The helical drive structure comprises a flange receivable in a slot such that when a thumb button is pushed into a finger grip, the hollow body slides along, and rotates relative to, the shaft. This movement of the hollow body causes the cutter on the end of the hollow body to rotate relative to the anvil located on the end of the shaft as the cutter slides past the anvil. This rotation of the cutter provides that the aortic punch can be used to achieve a clean and accurate cut to the wall of an aorta during heart surgery.

20 Claims, 5 Drawing Sheets

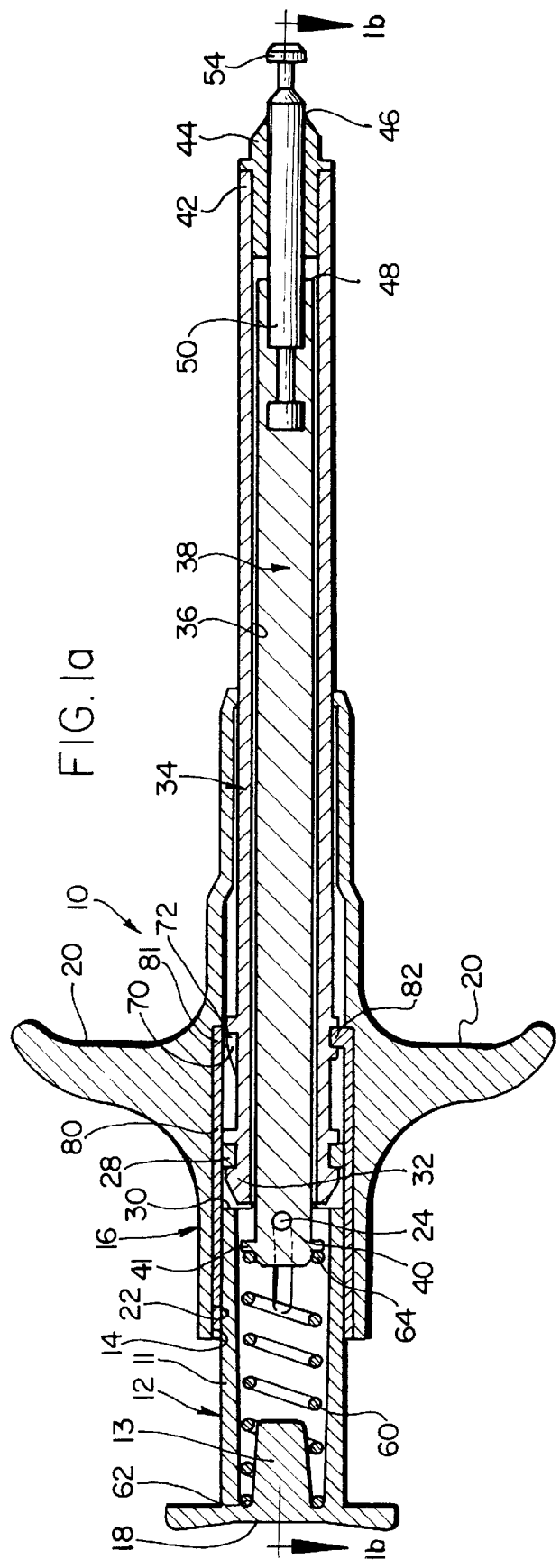
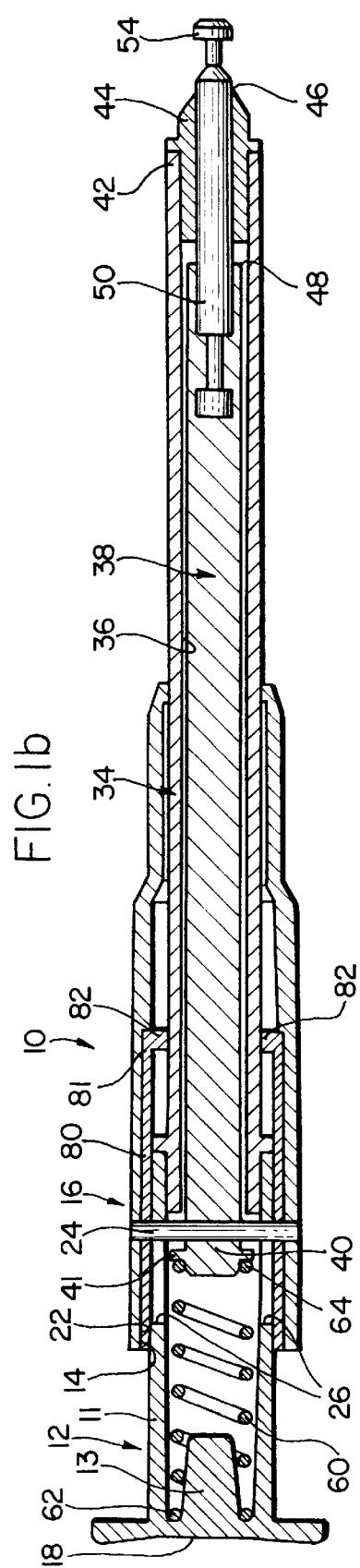

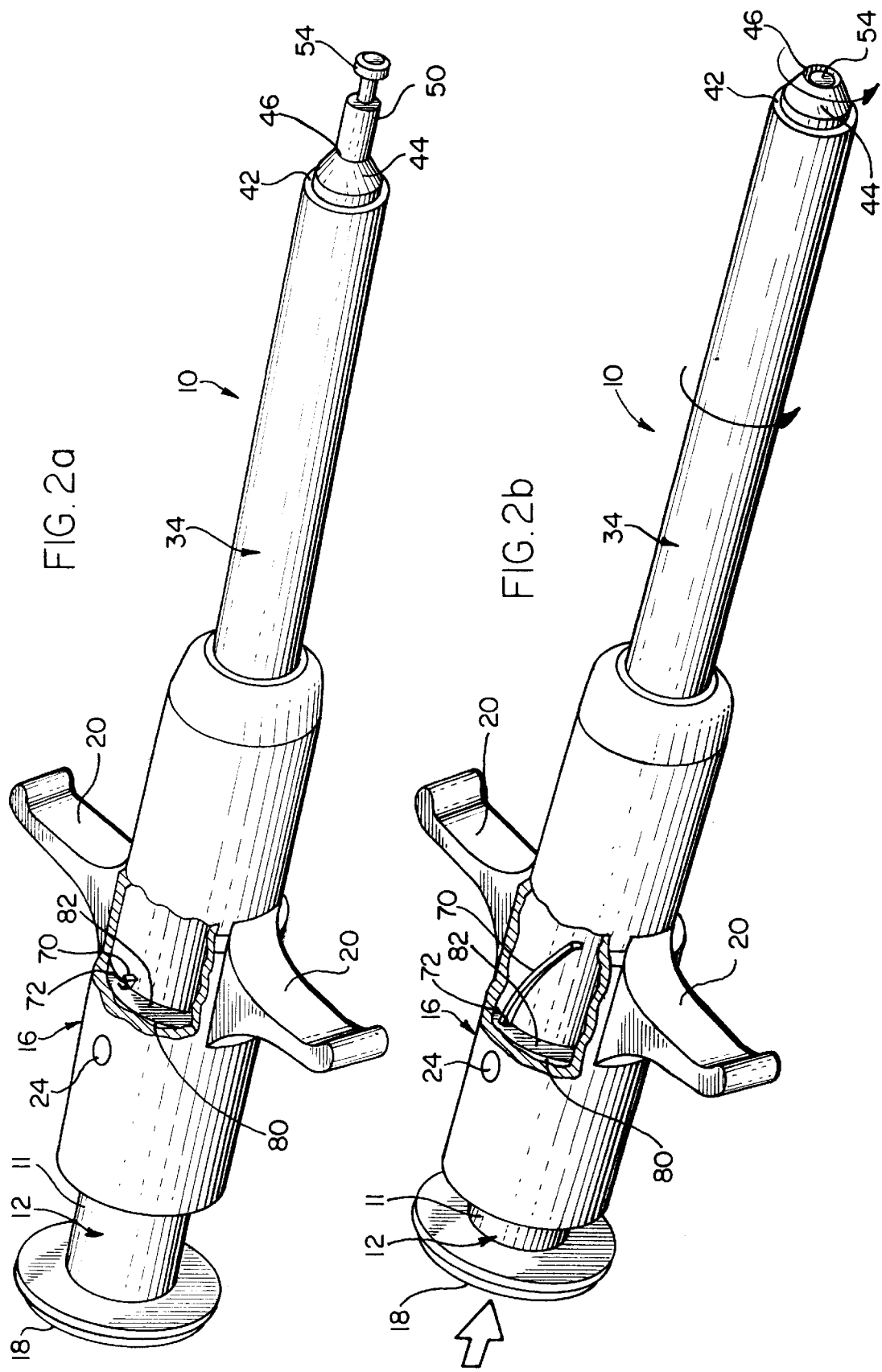

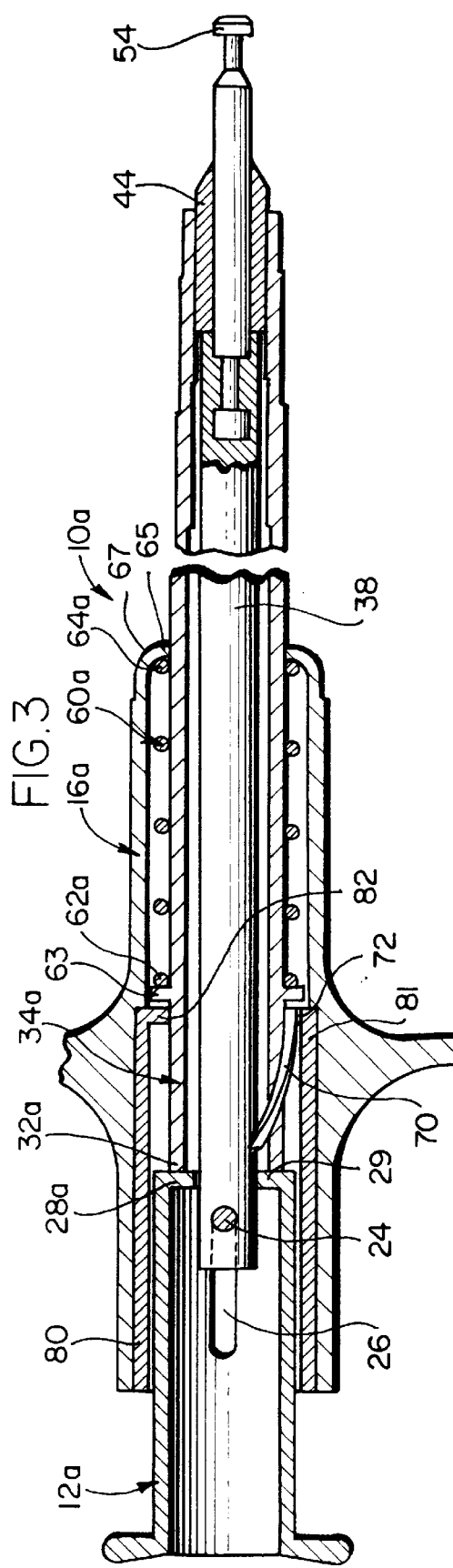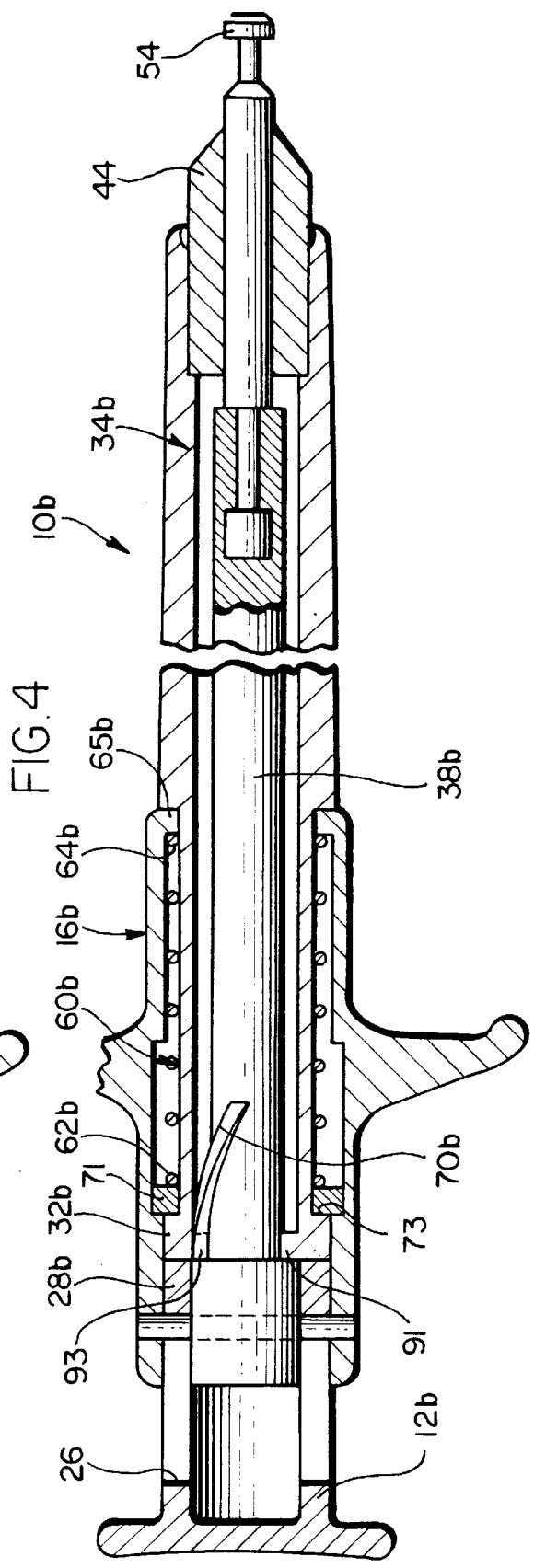

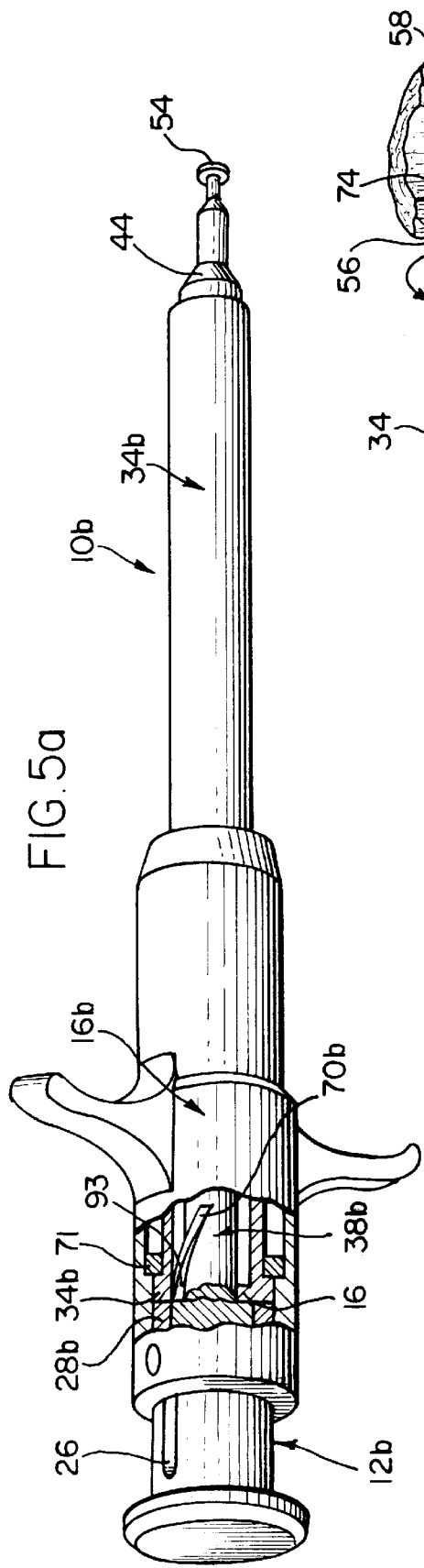
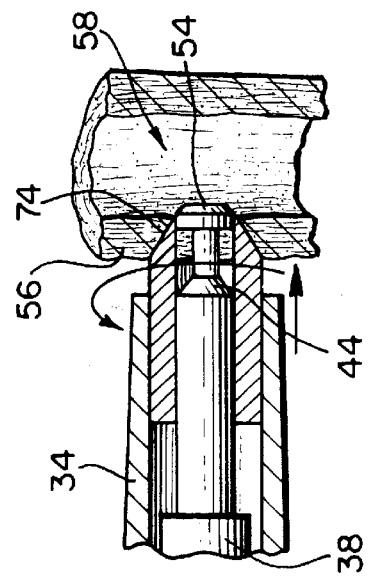
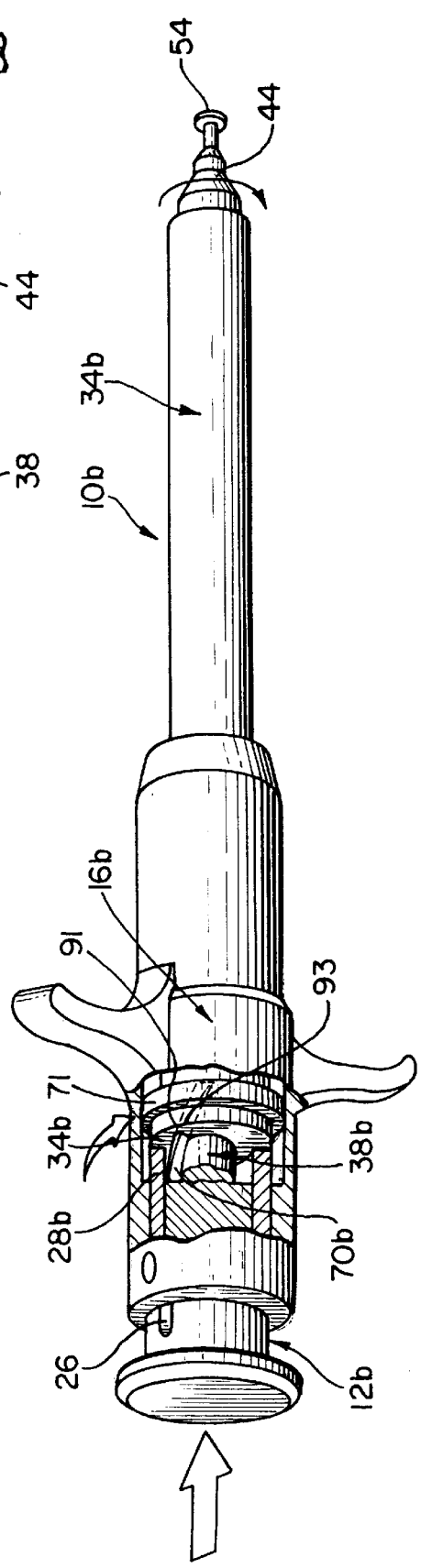
FIG. 5a
FIG. 6
FIG. 5b

ROTATING AORTIC PUNCH

BACKGROUND OF THE INVENTION

The present invention relates generally to aortic punches for use during heart surgery, and more specifically relates to a novel aortic punch having a rotating cutter.

Often the goal of heart surgery is to produce blood flow paths around the diseased areas of coronary arteries. To provide as such, saphenous vein grafts are used wherein an opening is formed in the wall of an ascending aorta, then a proximal end of a saphenous vein is anastomosed thereto. To form the opening in the wall of the aorta, an incision can be made using surgical scalpels and/or scissors. Then, an aortic punch can be used in order to attempt to obtain a clean, accurate somewhat larger opening in the aortic wall. Obtaining a clean and accurate opening is extremely important since an opening which is not formed cleanly and accurately often is frayed (albeit microscopically). As a result, the connection of the proximal end of the saphenous vein thereto may not be as reliable, and complications during or after surgery may result. Because heart surgery necessarily often entails the difference between life and death of the patient, it is extremely important to maximize the probability of success of every aspect of the surgical procedure. To this end, it is desirable to try to obtain as clean and as accurate an opening as possible in the wall of the aorta before grafting the saphenous vein thereto.

As mentioned, in attempting to obtain as accurate an opening as possible in the wall of the aorta, surgeons often utilize an aortic punch to form the opening. Typically, the aortic punch will include an anvil, or other support, which is first inserted into the aorta through a small incision in the wall. Then, the surgeon takes his or her hand and approximates the thumb and opposed first and second fingers to push a thumb button while pulling a cross-bar. Consequently, a cutting tube of the aortic punch extends, and slides around, the anvil, thus shearing a larger opening in the aortic wall. Finally, the anvil and cutting tube of the aortic punch are withdrawn from the incision in the wall of the aorta. Examples of prior art aortic punches can be found in the following U.S. Pat. Nos. 4,018,228; 4,216,776; 5,129, 913; 5,192,294; 5,403,338 and U.S. Design Pat. No. D372, 310.

Because the aortic punch accomplishes cutting the opening in the wall of the aorta by shearing, and effects this shearing by sliding the cutting tube past the anvil, the cut produced is not always extremely clean and accurate, and some fraying of the aortic wall may result. Moreover, because the aortic wall is extremely durable, the surgeon must typically exert a lot of hand pressure to successfully manipulate the aortic punch to shear the aortic wall. Finally, because shearing of the aortic wall is performed merely by axially sliding a cutting tube across an anvil, the cutting tube of the aortic punch does not remain sharp for very long. Therefore, the cutting tube must be sharpened often, or must be replaced frequently with a sharper cutting tube.

For the foregoing reasons, there is a need for an improved aortic punch which can be used to obtain a very clean and accurate opening in an aortic wall without any fraying, which can be used without having to exercise any excessive hand pressure, and which does not require that a cutting tube be sharpened or replaced very frequently. A much more effective aortic punch is an aortic punch designed and structured according to the present invention. The present invention is directed to substantially eliminate the difficulties encountered heretofore.

OBJECTS AND SUMMARY

Therefore, a general object satisfied by the claimed invention may be to provide an aortic punch which can be used to obtain a clean and accurate cut of an aortic wall with no fraying.

Another object satisfied by the claimed invention may be to provide an aortic punch which can be used without having to apply extensive hand pressure thereto.

Still another object satisfied by the claimed invention may be to provide an aortic punch which works in such a manner that a cutter of the aortic punch need not be replaced, or sharpened, as frequently.

Briefly, and in accordance with the foregoing, the present invention envisions an aortic punch comprising a rotatable hollow body member having a cutter on its end. A non-rotating member is adjacent the hollow body member, and the hollow body member is slidable relative to the non-rotating member. Helical drive structure is provided on the non-rotating member and the hollow body member, and the helical drive structure includes a helical drive flange on either member receivable in a slot provided on the other member. Relative axial movement of the hollow body member relative to the non-rotating member causes the helical drive flange and the slot to interact and move relative to the other causing the hollow body member to rotate relative to the non-rotating member and causing the cutter on the end of the hollow body to rotate.

A preferred embodiment of the present invention envisions an aortic punch comprising a thumb button pushable into a finger grip where the thumb button is securably engaged with a first end of a hollow body member. The finger grip has a pin secured therein, and the pin is received within a slot on the thumb button. A compression spring is located within the thumb button having a first end engaged with the thumb button and a second end engaged with a shaft. A cutter is on a second end of the hollow body member, and the hollow body member is slidable along the shaft. The shaft has an anvil at its end and is secured by the pin within the finger grip. On the hollow body member is a helical drive flange, and the helical drive flange is receivable in a slot on a sleeve which is also secured within the finger grip by the pin. The helical drive flange and the slot on the sleeve are shaped to provide that sliding the hollow body member along the shaft causes the helical drive flange to ride within the slot which results in the hollow body member rotating relative to the shaft and the cutter on the end of the hollow body member rotating relative to the anvil on the end of the shaft as the cutter moves past the anvil.

An alternative embodiment of the present invention envisions an aortic punch comprising a finger grip having a pin secured therein, a hollow body member having a first end and a second end, and a thumb button pushable into the finger grip and in contact with the first end of the hollow body member. The pin secured within the finger grip is received within a slot on the thumb button. A compression spring is located within the finger grip between an inwardly extending lip of the finger grip and an outwardly extending flange of the hollow body member. A cutter is on the second end of the hollow body member. A shaft is within the hollow body member, and the hollow body members slidable along the shaft. On the end of the shaft is an anvil. A sleeve is positioned within the finger grip, and the sleeve has a slot thereon. On the hollow body member is a helical drive flange which is receivable in the slot on the sleeve. The helical drive flange and the slot are shaped to provide that pushing the thumb button into the finger grip causes the”

helical drive flange to ride in the slot causing the hollow body member to slide and rotate along the shaft and causing the cutter on the end of the hollow body member to rotate relative to the anvil as the cutter moves past the anvil.

Still another embodiment of the present invention envisions an aortic punch comprising a finger grip with a pin secured therein. Pushable into the finger grip is a thumb button which has a slot that receives the pin secured within the finger grip. The thumb button is in contact with a first end of a hollow body member, and a compression spring is within the finger grip, located between an inwardly extending lip of the finger grip and a washer secured against an outwardly extending shoulder on the hollow body member. On the other end of the hollow body member is a cutter. The hollow body member is slidable along a shaft which is secured by the pin within the finger grip. An anvil is on the end of the shaft. Also on the shaft is a helical drive flange which is receivable in a slot on an inwardly extending shoulder of the hollow body member. The helical drive flange and the slot are shaped to provide that sliding the hollow body member along the shaft causes the slot to ride along the helical drive flange causing the hollow body member to slide and rotate relative to the shaft and causing the cutter on the end of the hollow body member to rotate relative to the anvil as it moves past the anvil.

BRIEF DESCRIPTION OF THE DRAWINGS

The organization and manner of the structure and function of the invention, together with further objects and advantages thereof, may be understood by reference to the following description taken in connection with the accompanying drawings, wherein like reference numerals identify like elements, and in which:

FIG. 1a is a cross-sectional view of a preferred embodiment aortic punch structured in accordance with the present invention;

FIG. 1b is a cross-sectional view, along line b—b, of the aortic punch shown in FIG. 1a;

FIG. 2a is a perspective view of the aortic punch of FIGS. 1a and 1b with a portion of a finger grip body cut-away to show a helical drive flange;

FIG. 2b is a perspective view of the aortic punch of FIG. 2a showing the helical drive flange riding in a slot as a thumb button is pushed;

FIG. 3 is a cross-sectional view of an alternative embodiment aortic punch structured in accordance with the present invention;

FIG. 4 is a cross-sectional view of another alternative embodiment aortic punch structured in accordance with the present invention;

FIG. 5a is a perspective view of the aortic punch of FIG. 4 with a portion of a finger grip body cut-away to show a helical drive flange;

FIG. 5b is a perspective view of the aortic punch of FIGS. 4 and 5a showing a slot riding along the helical drive flange as a thumb button is pushed;

FIG. 6 is a cross-sectional view of an anvil having been inserted through an incision in a wall of an aorta, and a rotating cutter proceeding to cut a portion of the wall to form a somewhat larger opening in the wall of the aorta.

DESCRIPTION OF EMBODIMENTS OF THE INVENTION

Figure 7A:
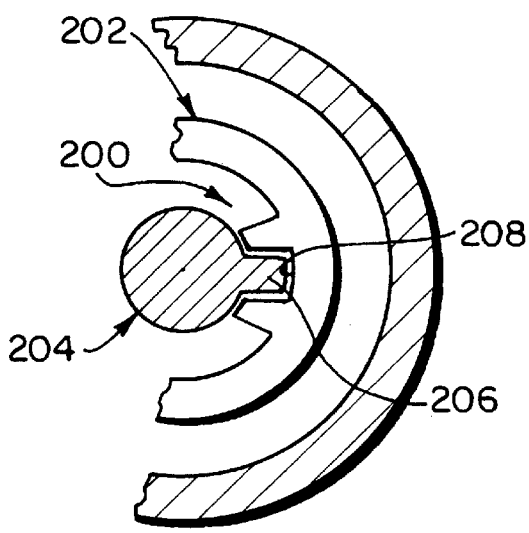
FIG. 7a–7d are simplified cross-sectional views illustrating different manners in which one may provide helical drive structure in accordance with the present invention.

While the present invention may be susceptible to embodiment in different forms, there is shown in the drawings, and herein will be described in detail, embodiments with the understanding that the present description is to be considered an exemplification of the principles of the invention and is not intended to limit the invention to that as illustrated and described herein.

Shown in the drawings are three aortic punches 10, 10a and 10b, each of which are structured in accordance with the present invention. FIGS. 1a, 1b, 2a and 2b depict a preferred embodiment aortic punch 10, FIG. 3 depicts an alternative embodiment aortic punch 10a, and FIGS. 4, 5a and 5b depict still another embodiment aortic punch 10b. For simplicity, where the structure of each of the aortic punches 10, 10a and 10b is identical, identical reference numerals are used within the drawings and the corresponding description.

The aortic punch 10 depicted in FIGS. 1a, 1b, 2a and 2b is the preferred embodiment of the present invention, and will now be described in detail. The aortic punch 10 is shaped and designed to be utilized by a surgeon using one of his or her hands. The aortic punch 10 includes a thumb button 12 pushable into a central opening 14 in a finger grip body 16 which is a non-rotating member. The thumb button 12 includes a thumb seat 18 which is shaped to be engaged by the thumb of the surgeon, and the thumb button 12 includes a hollow cylindrical portion 11 which extends into the central opening 14 of the finger grip body 16. The finger grip body 16 includes finger seats 20 which are shaped to be engaged by the first and second fingers of the surgeon. Walls 22 of the finger grip body 16 define the central opening 14 therein, and extending between, and secured to, the walls 22 of the finger grip body 16 is a pin 24, as shown in FIG. 1b. The pin 24 is received in slots 26 formed in the hollow cylindrical portion 11 of the thumb button 12. The slots 26 slide across the pin 24 when the thumb button 12 is pushed into the opening 14 of the finger grip 16. As the thumb button 12 is pushed into the opening 14 in the finger grip 16, the pin 24 restricts the extent to which the thumb button 12 can be pushed into the central opening 14.

As shown in FIG. 1a, a bottom portion 28 of the thumb button 12 has an opening 30 for snap-on, securable engagement with a top portion 32 of a hollow body member 34. This snap-on engagement provides that the hollow body member 34 moves along with the thumb button 12 when the thumb button 12 is pushed into, or pulled out from, the central opening 14 of the finger grip body 16.

The hollow body member 34 has a central throughbore 36 through which extends a shaft 38. As shown in FIG. 1b, the pin 24 extends through, and secures, a top portion 40 of the shaft 38. This securement of the pin 24 with the top portion 40 of the shaft 38 provides that the shaft 38 remains stationary with respect to the finger grip body 16 when the thumb button 12 is pushed into the central opening 14 in the finger grip body 16.

As shown in FIGS. 1a and 1b, within the thumb button 12 sits a compression spring 60. A top 62 of the compression spring 60 is engaged with a flange 13 within the hollow cylindrical portion 11 of the thumb button 12, and a bottom 64 of the compression spring 60 is engaged with a shoulder 41 on the top portion 40 of the shaft 38. The compression spring 60 works to urge the thumb button 12 out from the central opening 14 of the finger grip body 16 whenever the thumb button 12 is pushed therein. Providing the compressing spring 60 within the thumb button 12 permits the finger grip body 16 to be designed and shaped such that the finger seats 20 are relatively close together. As a result, the aortic punch 10 is easier to use because it more easily fits in the surgeon's hand.

As shown in FIG. 1b, the pin 24 within the finger grip body 16 also secures a non-rotating member, such as a sleeve 80 or helix follower, in place within the finger grip body 16. The sleeve 80 has a bottom portion 81 which forms an inwardly extending shoulder 82. The inwardly extending shoulder 82 of the sleeve 80 has opposing slots 72 formed thereon for receiving two opposing helical drive flanges 70 located on the hollow body member 34. The engagement of the helical drive flanges 70 within the slots 72 provides that the helical drive flanges 70 ride within the slots 72 whenever the thumb button 12 is pushed into the finger grip body 16. Pushing of the thumb button 12 into the finger grip body 16 is shown in the progression from FIG. 2a to FIG. 2b. As mentioned, when the thumb button 12 is pushed into the finger grip body 16, the shaft 38 does not move because the top portion 40 of the shaft is secured by the pin 24. However, the riding of the helical drive flanges 70 on the hollow body member 34 within the slots 72 on the stationary, non-rotating sleeve 80 provides that the hollow body member 34 rotates as the thumb button 12 is pushed. Also, the securable engagement of the bottom portion 28 of the thumb button 12 with the top portion 32 of the hollow body member 34 provides that the hollow body member 34 slides along the shaft 38 as the thumb button 12 is pushed. Therefore, the hollow body member 34 slides and rotates along the shaft 38, which remains stationary, whenever the thumb button 12 is pushed into the finger grip body 16.

As shown in FIGS. 1a, 1b, 2a and 2b, at the end 42 of the hollow body member 34 is a cutter 44 which preferably comprises a barrel pin having a sharp tip 46. Also, at the end 48 of the shaft 38 is secured a removable member 50 including an anvil 54. When the thumb button 12 is pushed into the central opening 14 of the finger grip body 16, the cutter 44 slides and rotates along with the hollow body member 34 in relation to the shaft 38 as the cutter 44 moves towards and across the anvil 54. Preferably, the cutter 44 rotates about 90° as the thumb button 12 is pushed into the finger grip body 16.

Preferably, the thumb button 12, finger grip body 16, and hollow body member 34 of the aortic punch 10 are all comprised of plastic, and the pin 24, shaft 38, compression spring 60, anvil member 50 (including the anvil 54), and the cutter 44 of the aortic punch 10 are all comprised of metal. However, these compositions are, of course, not imperative to the present invention.

While some reference was made to the general operation of the aortic punch 10 in order to adequately describe its structure, the operation and functioning of the aortic punch 10 will now be more fully described. To operate the aortic punch 10, a surgeon (not shown) would grab the aortic punch 10 in his or her hand, would place a thumb on the thumb seat 18 of the thumb button 12, and would place both an index finger tip and a middle finger tip on the finger seats 20 of the finger grip body 16. After a small incision 74 has been made in the wall 56 of the aorta 58, the surgeon would maneuver the aortic punch 10 so that the anvil 54 on the end of the shaft 38 is inserted into the incision 74, as shown in FIG. 6.

After the anvil 54 is inserted into the small incision 74 in the wall 56 of the aorta 58, the surgeon would push on the thumb seat 18, as shown in FIG. 2b, with his or her thumb while holding the finger seats 20 with his or her fingers. This pushing of the thumb button 12 drives the thumb button 12 into the central opening 14 in the finger grip body 16. As the thumb button 12 is pushed into the finger grip body 16, the slots 26 on the thumb button 12 ride along the pin 24 extending between the walls 22 of the finger grip 16.

Additionally, the hollow body member 34 slides along the shaft 38 because the top portion 32 of the hollow body member 34 is in securable, snap-on engagement with the opening 30 in the bottom portion 28 of the thumb button 12. As the thumb button 12 is pushed into the finger grip 16, the compression spring 60 compresses within the thumb button 12 against the shaft 38, and the shaft 38 remains stationary because of securement by the pin 24 within the finger grip 16. Since the hollow body member 34 slides along the shaft 38, the cutter 44 at the end 42 of the shaft 38 moves toward the anvil 54 at the end 52 of the shaft 38, and this is shown in the progression from FIG. 2a to FIG. 2b.

When the thumb button 12 is pushed into the opening 14 in the finger grip body 16, the non-rotating sleeve 80 within the finger grip body 16 also remains stationary because of securement by the pin 24. At this time, the helical drive flanges 70 on the hollow body member 34 ride within the slots 72 on the inwardly extending shoulder 82 of the sleeve 80, as shown in the progression from FIG. 2a to FIG. 2b. Therefore, as the thumb button 12 is pushed, the hollow body member 34 slides and rotates along the shaft 38, and the cutter 44 on hollow body member 34 slides towards, and rotates relative to, the anvil 54. As the thumb button 12 is more fully pushed, the cutter 44 rotates and slides past the anvil 54, as shown in FIG. 6, thus severing a portion 57 of the wall 56 of the aorta 58. At this time, the aortic punch 10 can be withdrawn from the incision 74 such that the anvil 54, the cutter 44 and the severed portion 57 are collectively withdrawn. Then, the thumb button 12 can be released, and the compression spring 60 urges the thumb button 12 from the finger grip body 16. Thus, the cutter 44 rotates and retracts from the anvil 54 causing the severed portion 57 of the aortic wall 56 to drop away from the aortic punch 10.

Should the severed portion 57 of the wall 56 get caught between the anvil 54 and the cutter 44, thus jamming the aortic punch 10, the structure of the preferred embodiment aortic punch 10 provides that the surgeon can pull on the thumb button 12 to release the severed portion 57. Because the thumb button 12 is in snap-on, securing engagement with the hollow body member 34, pulling the thumb button 12 causes the hollow body member 34 to slide in relation to the shaft 38. Additionally, much like when the thumb button 12 was pushed, the interaction of the helical drive flanges 70 with the slots 72 causes the hollow body member 34 to rotate as it slides along the shaft 38. Therefore, the cutter 44 rotates and slides away from the anvil 54 when the thumb button 12 is pulled. Consequently, pulling the thumb button 12 from the finger grip 16 should cause the severed portion 57 to dislodge from between the anvil 54 and the cutter 44, and drop away from the aortic punch 10.

Because the aortic punch 10 provides that the cutter 44 rotates as it slides by the anvil 54, a cleaner and more accurate cut is achieved than if the cutter 44 were merely slid by the anvil 54 without rotating. Additionally, the rotation of the cutter 44 helps cut through the wall 56; therefore, cutting is more readily achieved by the aortic punch 10 without the surgeon having to exercise any extensive hand pressure. Further, because the rotation of the cutter 44 assists in the cut, the cutter 44 remains sharper, for a longer period of time, through more iterations.

As mentioned, an alternative embodiment aortic punch 10a is depicted in FIG. 3. This alternative embodiment aortic punch 10a will now be described. Much like the preferred embodiment aortic punch 10, the alternative embodiment aortic punch 10a is shaped and designed to be utilized by a surgeon and includes a thumb button 12a pushable into a finger grip body 16a which is a non-rotating member. Within the finger grip body 16a extends a pin 24 much like in the preferred embodiment, and the pin 24 is received in slots 26 in the thumb button 12a. A bottom portion 28a of the thumb button 12a forms an inwardly extending lip 29 which is in contact with the top portion 32a of the hollow body member 34a. This contact between the thumb button 12a and the hollow body member 34a provides that the hollow body member 34a moves along with the thumb button 12a when the thumb button 12a is pushed into the finger grip body 16a. Much like with the preferred embodiment, a shaft 38 extends through the hollow body member 34a, and is secured by the pin 24. This securement, as with the preferred embodiment, provides that the shaft 38 remains stationary with respect to the finger grip body 16a when the thumb button 12a is pushed.

Within the finger grip 16a sits a compression spring 60a. A top 62a of the compression spring 60a is engaged with an outwardly extending flange 63 on the hollow body member 34a, and a bottom 64a of the compression spring 60a is engaged with an inwardly extending lip 65 at the bottom 67 of the finger grip body 16a.

Much like the preferred embodiment, the pin 24 of the alternative embodiment aortic punch 10a secures a non-rotating member or helix follower, such as a sleeve 80 in place, and the sleeve 80 has a bottom portion 81 which forms an inwardly extending shoulder 82. The inwardly extending shoulder 82 of the sleeve 80 has two opposing slots 72 formed thereon for receiving two opposing helical drive flanges 70 located on the hollow body member 34a, and the engagement of the helical drive flanges 70 within the slots 72 provides that the helical drive flanges 70 ride within the slots 72 whenever the thumb button 12a is pushed into the finger grip body 16a, in identical fashion as is shown in FIGS. 2a to FIG. 2b with respect to the preferred embodiment. The riding of the helical drive flanges 70 on the hollow body member 34a within the slots 72 on the stationary, non-rotating sleeve 80 provides that the hollow body member 34a rotates as the thumb button 12a is pushed. When the hollow body member 34a rotates, the thumb button 12a acts as a thrust bearing for the hollow body member 34a. Additionally, as shown, the bottom portion 81 of the sleeve 80 abuts the outwardly extending flange 63 on the hollow body member 34a when the thumb button 12a is not punched; therefore, the sleeve 80 serves as a stop to arrest further upward travel of the hollow body member 34a.

The alternative embodiment aortic punch 10a also includes a cutter 44 and an anvil 54 so that when the thumb button 12a is pushed into the finger grip 16a, the cutter 44 slides and rotates along with the hollow body member 34a as the cutter 44 moves towards and across the anvil 54. Like with the preferred embodiment, preferably the thumb button 12a, finger grip 16a, and hollow body member 34a of the aortic punch 10a are all comprised of plastic, and the pin 24, shaft 38, compression spring 60a, anvil 54, and cutter 44 are all comprised of metal.

To operate the alternative embodiment aortic punch 10a, a surgeon would grab the aortic punch 10a in his or her hand and insert the anvil 54 into an incision 74, as shown in FIG. 6. Then, the surgeon would push on the thumb button 12a causing the hollow body member 34a to slide along the shaft 38 because the bottom portion 28a of the thumb button 12a is in contact with the hollow body member 34a. As the thumb button 12a is pushed, the compression spring 60a compresses within the finger grip 16a. Since the hollow body member 34a slides along the shaft 38, the cutter 44 moves toward the anvil 54.

When the thumb button 12a is pushed, the non-rotating sleeve 80 remains stationary because of securement by the pin 24, and the helical drive flanges 70 ride along the slots 72 on the inwardly extending shoulder 82 of the sleeve 80. Therefore, as the thumb button 12a is pushed, the hollow body member 34a slides and rotates along the shaft 38, and the cutter 44 slides towards, and rotates relative to, the anvil 54. As the thumb button 12a is more fully pushed, the cutter 44 rotates and slides past the anvil 54, as shown in FIG. 6, thus severing a portion 57 of the wall 56 of the aorta 58. At this time, the aortic punch 10a can be withdrawn from the incision 74 such that the anvil 54, the cutter 44 and the severed portion 57 are collectively withdrawn. Then, the thumb button 12a can be released, and the compression spring 60a urges the thumb button 12a from the finger grip 16a. Thus, the cutter 44 retracts from the anvil 54 causing the severed portion 57 to drop away from the aortic punch 10a.

As mentioned, both of the aortic punches 10 and 10a provide that the cutter 44 rotates as it slides by the anvil 54. To provide as such, the aortic punches 10, 10a provide that a hollow body member 34, 34a rotates as it moves axially. To provide this rotation of the hollow body 34, 34a upon axial movement, the aortic punches 10, 10a include helical drive structure between the hollow body member 34, 34a and an adjacent non-rotating member, namely, a sleeve 80. Specifically, the aortic punches 10, 10a provide a helical drive flange 70 on the hollow body member 34, 34a and a slot 72 on the sleeve 80. One skilled in the art would recognize that there are many alternative ways to provide that helical drive structure causes the hollow body member 34 to rotate when it moves axially. One example of such is the aortic punch 10b depicted in FIGS. 4, 5a and 5b, and this embodiment will now be described.

Like the other embodiments, the aortic punch 10b includes a thumb button 12b pushable into a finger grip 16b which is a non-rotating member. A pin 24 extends within the finger grip 16b and is received in slots 26 in the thumb button 12b. The pin 24 secures a shaft 38b within the finger grip body 16b and within hollow body member 34b.

Much like with the aortic punch 10a shown in FIG. 3, the bottom portion 28b of the thumb button 12b of the aortic punch 10b is in contact with a top portion 32b of a hollow body member 34b, and this contact provides that the hollow body member 34b moves along with the thumb button 12b when the thumb button 12b is pushed into the finger grip body 16b.

Within the finger grip body 16b sits a compression spring 60b. A top 62b of the compression spring 60b is engaged with a thrust washer 71 which is in contact with an outwardly extending shoulder 73 on the hollow body member 34b, and a bottom 64b of the compression spring 60b is engaged with an inwardly extending lip 65b of the finger grip body 16b. As with the other embodiments, the compression spring 60b works to urge the thumb button 12b out from the finger grip body 16b whenever the thumb button 12b is pushed therein.

The helical drive structure of the aortic punch 10b will now be decribed. As shown in FIGS. 4, 5a and 5b, hollow body member 34b has an inwardly extending shoulder 91 which has slots 93 thereon for engaging helical drive flanges 70b (only one shown) located on the shaft 38b. The engagement of the helical drive flanges 70b within the slots 93 provides that the slots 93 ride along the helical drive flanges 70b whenever the thumb button 12b is pushed into the finger grip body 16b. This movement of the slots 93 along the helical drive flanges 70b is shown in the progression from FIG. 5a to FIG. 5b. When the thumb button 12b is pushed into the finger grip 16b, the shaft 38b does not move because the shaft 38b is secured by the pin 24. However, the riding of the slots 93 on the hollow body member 34b along the helical drive flanges 70b on the shaft 38b provides that the hollow body member 34b rotates in relation to the shaft 38b as the thumb button 12b is pushed. Also, the contact between the thumb button 12b and the hollow body member 34b provides that the hollow body member 34b slides along the shaft 38b as the thumb button 12b is pushed. Therefore, the hollow body member 34b slides and rotates along the shaft 38b, which remains stationary, whenever the thumb button 12b is pushed into the finger grip body 16b. When the hollow body member 34b rotates, the thumb button 12b acts as a thrust bearing for the hollow body member 34b.

As with the other embodiments, the aortic punch 10b includes a cutter 44 and an anvil 54, and when the thumb button 12b is pushed into the finger grip 16b, the cutter 44 slides and rotates as the cutter 44 moves towards and across the anvil 54.

As with the other embodiments, preferably, the thumb button 12b, finger grip 16b, and hollow body member 34b of the aortic punch 10b are all comprised of plastic, and the pin 24, shaft 38b, compression spring 60b, anvil 54, and the cutter 44 are all comprised of metal.

The operation and functioning of this embodiment aortic punch 10b will now be more fully described. To operate the aortic punch 10b, a surgeon (not shown) would grab the aortic punch 10b in his or her hand, and would insert the anvil 54 into an incision 74, as shown in FIG. 6. After the anvil 54 is inserted, the surgeon would push the thumb button 12b causing the slot 93 in the hollow body member 34b to slide along the shaft 38b as shown in FIG. 5b. As the thumb button 12b is pushed, the compression spring 60b compresses within the finger grip 16b, and the shaft 38b remains stationary because of securement by the pin 24 within the finger grip 16b. Since the hollow body member 34b slides along the shaft 38b, the cutter 44 moves toward the anvil 54.

When the thumb button 12b is pushed, the slots 93 on the hollow body member 34b ride along the helical drive flanges 70b on the shaft 38b. Therefore, as the thumb button 12b is pushed, the hollow body member 34b slides and rotates along the shaft 38, and the cutter 44 on the hollow body member 34b slides towards, and rotates relative to, the anvil 54. As the thumb button 12b is more fully pushed, the cutter 44 rotates and slides past the anvil 54, as shown in FIG. 6, thus severing a portion 57 of the wall 56 of the aorta 58. At this time, the aortic punch 10b can be withdrawn from the incision 74 such that the anvil 54, the cutter 44 and the severed portion 57 are collectively withdrawn. Then, the thumb button 12b can be released, and the compression spring 60b urges the thumb button 12b from the finger grip 16b. Thus, the cutter 44 retracts from the anvil 54 causing the severed portion 57 to drop away from the aortic punch 10b.

Figure 7B:
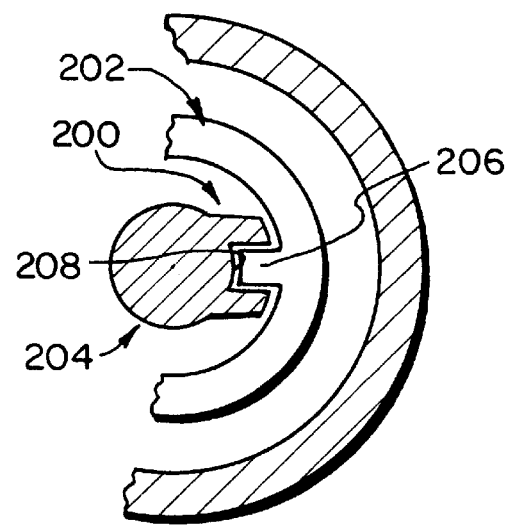
Figure 7C:
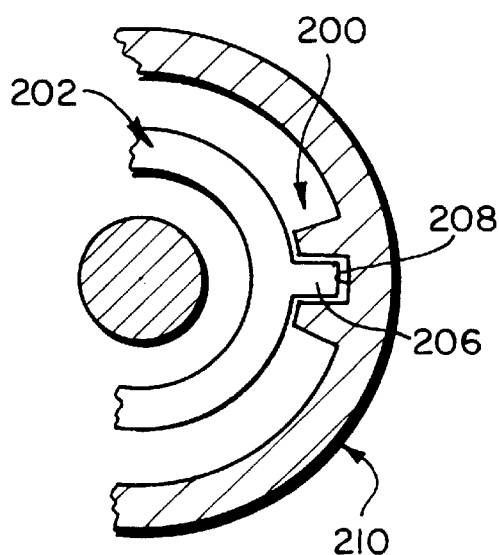
Figure 7D:
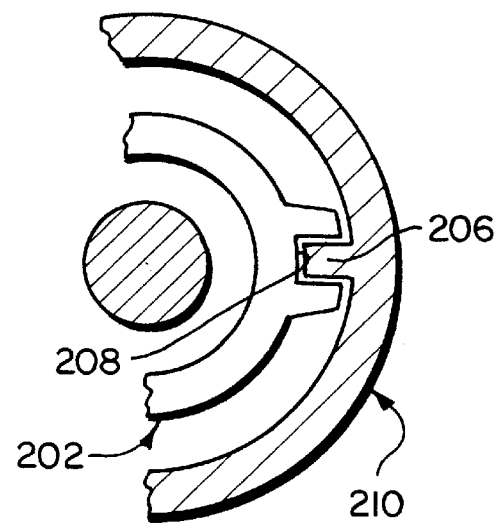

All three aortic punches 10, 10a and 10b provide that a hollow body member rotates because of the interaction of helical drive structure, and more specifically because of the interaction of a helical drive flange and a slot. While one of the helical drive flange or slot is preferably on the hollow body member, the other of the helical drive flange or slot can be provided on practically any adjacent non-rotating member. For example, as shown in FIGS. 7a and 7b, helical drive structure 200 can be provided between a hollow body member 202 and an adjacent non-rotating body member such as a shaft 204. Specifically, as shown in FIG. 7a, a helical drive flange 206 can be provided on the shaft 204, and a slot 208 can be provided on the hollow body member 202 where the slot 208 rides along the helical drive flange 204 as the hollow body member moves axially. As a result, the hollow body member 202 rotates as it moves axially. This type of helical drive structure is that which is provided on the aortic punch 10b shown in FIGS. 4, 5a and 5b. Alternatively, as shown in FIG. 7b, it is possible to provide that the helical drive structure 200 between the hollow body member 202 and an adjacent non-rotating body member such as a shaft 204 comprises a helical drive flange 206 on the hollow body member 202 and a slot 208 on the shaft 204 where the helical drive flange 206 rides within the slot 208 as the hollow body member 202 moves axially. Still further, it is possible, as shown in FIG. 7c and 7d, to provide helical drive structure 200 between the hollow body member 202 and another adjacent non-rotating body member such as a sleeve 210 secured to a finger grip body (not shown). For example, as shown in FIG. 7c, it is possible to provide that the helical drive structure comprises a helical drive flange 206 on the hollow body member 202 and a slot 208 on the sleeve 204 where the helical drive flange 206 rides within the slot 208 as the hollow body member 202 moves axially. This type of helical drive structure is included on the aortic punches 10 and 10a shown in FIGS. 1, 2 and 3. Alternatively, as shown in FIG. 7d, the helical drive structure 200 between the hollow body member 202 and another adjacent non-rotating body member such as a sleeve 210 can comprise a helical drive flange 206 on the sleeve 210 and a slot 208 on the hollow body member 202 where the slot 208 rides along the helical drive flange 200.

It is not important to the present invention that the helical drive structure be provided on any specific elements of an aortic device. What is important to the present invention is that the helical drive structure is provided on the aortic punch in such a manner that the cutter will rotate as it slides by the anvil. Therefore, while several embodiments of the present invention are shown and described herein, it is envisioned that those skilled in the art may devise various modifications and equivalents without departing from the spirit and scope of the invention as defined by the appended claims. For example, it is possible to provide a helical drive flange on a hollow body, and provide a slot which receives the helical drive flange directly upon the finger grip body. Because modifications such as this are possible without departing from the spirit and scope of the present invention, the present invention is not intended to be limited by the foregoing disclosure.

The invention claimed is:

1. An aortic punch comprising:

a rotatable hollow body member having an end;

a cutter on said end of said hollow body;

a non-rotating member adjacent said hollow body, said hollow body slidable relative to said non-rotating member; and helical drive structure on said non-rotating member and said hollow body member, said helical drive structure including a helical drive flange on one of said members, said helical drive flange receivable in a slot provided on the other of said members, wherein relative axial movement of said hollow body member relative to said non-rotating member causes said helical drive flange and said slot to interact and move relative to each other causing said hollow body member to rotate relative to said non-rotating member and causing said cutter on said end of said hollow body to rotate.

2. The aortic punch as defined in claim 1, wherein said punch comprises a non-rotating shaft having an anvil on one end of said non-rotating shaft for cooperation with said cutter and a non-rotating body element affixed to said non-rotating shaft, one or the other of which provides said non-rotating member upon which a component of said helical drive structure is provided.

3. The aortic punch as defined in claim 2, said helical drive structure comprising a helical drive flange on one of said shaft and said hollow body member, said helical drive flange receivable in a slot provided by the other of said shaft or said hollow body member, wherein sliding said hollow body member along said shaft causes one of said helical drive flange and said slot to move relative to each other causing said hollow body member to rotate relative to said shaft and causing said cutter on said end of said hollow body to rotate relative to said anvil on said end of said shaft as said cutter moves past said anvil.

4. The aortic punch as defined in claim 2, said helical drive structure comprising a helical drive flange on one of said non-rotating body element and said hollow body member, said helical drive flange receivable in a slot provided by the other of said non-rotating body element or said hollow body member, wherein sliding said hollow body member along said shaft causes one of said helical drive flange and said slot to move relative to the other causing said hollow body member to rotate relative to said shaft and causing said cutter on said end of said hollow body to rotate relative to said anvil on said end of said shaft as said cutter moves past said anvil.

5. The aortic punch as defined in claim 4, said non-rotating body element comprising a sleeve secured to a finger grip, said aortic punch further comprising a thumb button pushable into said finger grip, wherein said thumb button is securably engaged with said hollow body member, and wherein said thumb button pushes said hollow body member causing said hollow body member to slide along said shaft when said thumb button is pushed into said finger grip.

6. The aortic punch as defined in claim 5, further comprising a pin secured within said finger grip, wherein said pin secures said shaft, and wherein said pin is received in a slot on said thumb button.

7. The aortic punch as defined in claim 6, further comprising a compression spring within said thumb button, said spring having a first end engaged with said thumb button and having a second end engaged with said shaft.

8. The aortic punch as defined in claim 7, wherein said thumb button pulls on said hollow body member causing said hollow body member to slide and rotate along said shaft when said thumb button is pulled from said finger grip.

9. The aortic punch as defined in claim 5, further comprising a compression spring within said thumb button, said spring having a first end engaged with said thumb button and having a second end engaged with said shaft.

10. The aortic punch as defined in claim 9, wherein said thumb button pulls on said hollow body member causing said hollow body member to slide and rotate along said shaft when said thumb button is pulled from said finger grip.

11. The aortic punch as defined in claim 5, wherein said thumb button pulls on said hollow body member causing said hollow body member to slide and rotate along said shaft when said thumb button is pulled from said finger grip.

12. The aortic punch as defined in claim 5, further comprising a compression spring located between an inwardly extending lip of said finger grip and an outwardly extending flange on said hollow body member.

13. The aortic punch as defined in claim 5, wherein said helical drive flange is on said hollow body member and said slot is on said sleeve.

14. The aortic punch as defined in claim 13, wherein said slot is on an inwardly extending shoulder of said sleeve.

15. The aortic punch as defined in claim 2, wherein said helical drive flange is on said shaft and said slot is on said hollow body member.

16. The aortic punch as defined in claim 15, wherein said slot is on an inwardly extending shoulder of said hollow body member.

17. The aortic punch as defined in claim 15, further comprising a compression spring within said finger grip, said compression spring located between an inwardly extending lip of said finger grip and a washer engaged against an outwardly extending shoulder on said hollow body member.

18. An aortic punch comprising:
a finger grip;
a pin secured within said finger grip;
a hollow body having a first end and a second end;
a thumb button having a slot thereon, said thumb button in contact with said first end of said hollow body, said thumb button pushable into said finger grip, said pin secured within said finger grip received within said slot on said thumb button;
a compression spring within said finger grip, said compression spring located between an inwardly extending lip of said finger grip and a washer engaged against an outwardly extending shoulder on said hollow body;
a cutter on said second end of said hollow body;
a shaft within said hollow body, said shaft having an end, said pin securing said shaft, said hollow body slidable along said shaft;
an anvil on said end of said shaft; and
a helical drive flange on said shaft, said helical drive flange receivable in a slot on an inwardly extending shoulder of said hollow body, wherein said helical drive flange and said slot on said hollow body are shaped to provide that sliding said hollow body along said shaft causes said slot on said hollow body to ride along said helical drive flange on said shaft causing said hollow body to rotate relative to said shaft and causing said cutter on said end of said hollow body to rotate relative to said anvil on said end of said shaft as said cutter moves past said anvil.

19. An aortic punch comprising:
a finger grip;
a pin secured within said finger grip;
a hollow body having a first end and a second end;
a shaft within said hollow body and secured by said pin, said shaft having an end, said hollow body slidable along said shaft;
a thumb button having a slot thereon, said thumb button securably engaged with said first end of said hollow body, said thumb button pushable into said finger grip, said pin secured within said finger grip received within said slot on said thumb button, wherein said thumb button pushes said hollow body causing said hollow body to slide along said shaft when said thumb button is pushed into said finger grip;
a compression spring within said thumb button, said compression spring having a first end engaged with said thumb button and having a second end engaged with said shaft;

a cutter on said second end of said hollow body;

an anvil on said end of said shaft;

a sleeve secured within said finger grip by said pin, said sleeve having a slot thereon; and a helical drive flange on said hollow body, said helical drive flange receivable in said slot on said sleeve within said finger grip, wherein said helical drive flange and said slot are shaped to provide that sliding said hollow body along said shaft causes the helical drive flange to ride in the slot causing said hollow body to rotate relative to said shaft and causing said cutter on said end of said hollow body to rotate relative to said anvil blade on said end of said shaft as said cutter moves past said anvil.

20. The aortic punch as defined in claim 18, wherein said thumb button pulls on said hollow body member causing said hollow body member to slide and rotate along said shaft when said thumb button is pulled from said finger grip.

* * * * *